United States Patent [19]

Long

[11] Patent Number: 6,017,350
[45] Date of Patent: Jan. 25, 2000

[54] PRESSURIZER APPARATUS

[75] Inventor: Jack F. Long, Warsaw, Ind.

[73] Assignee: DePuy Orthopaedics, Inc., Warsaw, Ind.

[21] Appl. No.: 08/942,969

[22] Filed: Oct. 3, 1997

[51] Int. Cl.⁷ .................................................. A61B 17/58
[52] U.S. Cl. ............................................................ 606/94
[58] Field of Search ................................. 606/92, 93, 94, 606/95, 86

[56] References Cited

U.S. PATENT DOCUMENTS

| | | |
|---|---|---|
| 4,274,163 | 6/1981 | Malcom et al. . |
| 4,302,855 | 12/1981 | Swanson . |
| 4,338,925 | 7/1982 | Miller . |
| 4,344,190 | 8/1982 | Lee et al. . |
| 4,357,716 | 11/1982 | Brown . |
| 4,462,394 | 7/1984 | Jacobs . |
| 4,466,435 | 8/1984 | Murray . |
| 4,488,549 | 12/1984 | Lee et al. . |
| 4,523,587 | 6/1985 | Frey . |
| 4,627,434 | 12/1986 | Murray . |
| 4,645,504 | 2/1987 | Byers . |
| 4,745,914 | 5/1988 | Frey et al. . |
| 4,815,454 | 3/1989 | Dozier, Jr. . |
| 4,881,536 | 11/1989 | Noble et al. . |
| 4,896,662 | 1/1990 | Noble . |
| 4,950,295 | 8/1990 | Weigum et al. . |
| 4,997,448 | 3/1991 | Filer . |
| 5,009,666 | 4/1991 | Van Syckle et al. . |
| 5,061,287 | 10/1991 | Feiler . |
| 5,078,746 | 1/1992 | Garner . |
| 5,370,702 | 12/1994 | Jones . |
| 5,383,932 | 1/1995 | Wilson et al. . |
| 5,480,453 | 1/1996 | Burke . |
| 5,501,687 | 3/1996 | Willert et al. . |
| 5,507,748 | 4/1996 | Sheehan et al. . |
| 5,507,749 | 4/1996 | Draenert . |
| 5,741,265 | 4/1998 | Chan .......................................... 606/94 |
| 5,800,439 | 9/1998 | Clyburn .................................... 606/94 |

FOREIGN PATENT DOCUMENTS

| | | |
|---|---|---|
| 0073604A1 | 3/1983 | European Pat. Off. . |
| 1430083 | 3/1976 | United Kingdom . |

OTHER PUBLICATIONS

Catalog: "Composite The Zimmer® Bone Cement System" pp. 1–18, Zimmer, Inc., date unknown.

Catalog: "Richards Brings You The Cemented Modular Hip System Spectron®", Richards Modular System, Richards Medical Company, 1987.

"High Vacuum Cement Injection System Third Generation Cementing Technique", Stryker® Instruments, No. 1000–119, Feb. 1995, Rev. B.

Catalog:"Buck Cement Restrictor Bone Cement Accessory System", Smith & Nephew, 1995.

*Primary Examiner*—Michael Buiz
*Assistant Examiner*—(Jackie)Tan-Uyen T. Ho

[57] ABSTRACT

A pressurizer apparatus for substantially sealing proximal ends of prepared medullary canals during pressurization with a cement injection device, comprising a body portion including dissimilar surfaces on opposed ends formed to engage the proximal ends and with each surface including dissimilar surfaces and a dissimilar-surface channel extending between the dissimilar surfaces and wherein the dissimilar-surface channel is sized and adapted to receive at least a portion of the cement injection device therein from either end of the channel

20 Claims, 5 Drawing Sheets

FIG. 17

PRESSURIZER APPARATUS

BACKGROUND AND SUMMARY OF INVENTION

The present invention relates to a pressurizer apparatus. More particularly, the present invention relates to a pressurizer apparatus for use in hip replacement surgery on a prepared medullary canal of a patient's femur during pressurization of bone cement injected into the prepared medullary canal.

Surgeons often pressurize bone cement during a prosthetic implant surgery to provide a cement mantle. See, for example, U.S. Pat. No. 4,488,549 entitled "Pressurization of Cement in Bones", to Lee et al. Such pressurization interdigitates the bone cement into the cancellous bone structure to increase the effectiveness of the cement mantle in which the prosthetic implant is placed. Surgeons also often prepare a bone, such as a femur during hip replacement surgery, for receiving the pressurized cement by first removing a head of the femur leaving an opening at a proximal end and then reaming the medullary canal. Surgeons have also used conventional sealing members to occlude the proximal end of the femur to obtain pressurization of the cement and the femur. See for example U.S. Pat. No. 4,815,454 entitled "Apparatus and Method for Injecting Bone Cement" to Dozier, Jr. Pressurization of the bone cement increases penetration of cement into the bone and creates a bone/cement interface to securely hold the prosthetic device in place.

Because patients' femurs are of various sizes, the proximal ends of prepared medullary canals also vary in size. It can be difficult for a surgeon to manipulate a single conventional sealing member to achieve a suitable seal with a variety of prepared medullary canals. Therefore, it can be necessary to have multiple conventional sealing members of various shapes and sizes present in the operating room to permit a surgeon or other medical personnel to select the appropriately sized conventional sealing member for a particular medullary canal. The presence of multiple differently sized conventional sealing member in the surgery room during hip replacement surgery can clutter the operating area. Handling multiple conventional sealing members can also be cumbersome to the surgeon. Furthermore, manufacturing multiple conventional sealing members and shipping the same to a location of the surgery can produce additional production and shipping costs.

What is needed is a pressurizer apparatus that is suitable for use on a number of shapes and size ranges of prepared medullary canals to seal the prepared canal during pressurization with a cement injection device.

According to the present invention, a pressurizer apparatus that is suitable for substantially sealing a prepared medullary canal having a proximal end during pressurization with a cement injection device is provided. The pressurizer apparatus comprises a body portion that includes dissimilar surfaces formed to engage the proximal end of the prepared medullary canal and to cover the medullary canal and a dissimilarsurface channel extending between the dissimilar surfaces. The dissimilar-surface channel is sized to receive at least a portion of the cement injection device therein to form a substantial seal between the medullary canal and the body portion.

According to another embodiment of the present invention, a pressurizer apparatus that is suitable for substantially sealing a prepared medullary canal having a proximal end and an outer lip extending about the medullary canal adjacent the proximal end during pressurization of the prepared medullary canal with a cement injection device having a guide portion is provided. The pressurizer apparatus comprises a one-piece body portion that includes a generally convex-shaped first surface formed to engage the lip, a second surface spaced apart from the first surface, and a channel extending between the first surface and the second surface. The channel is sized to receive the guide portion of the cement injection device therethrough.

According to yet another embodiment of the present invention, a pressurizer apparatus that is suitable for use with a cement injection device having a guide portion to substantially seal proximal ends of prepared medullary canals during pressurization of the prepared medullary canals is provided. The pressurizer apparatus comprises a body portion that includes an exterior surface formed to engage the proximal end and an inner surface that defines a first wall having a first diameter, a second wall having a second diameter that is greater than the first diameter, and at least one channel that extends through the exterior surface and incorporates the first and second walls. The second wall has a first end, a second end spaced apart from the first end, and a tab formed for engagement with the guide portion and that extends into the channel and is positioned to lie between the first and second ends of the second wall.

According to still another embodiment of the present invention, a method of sealing a prepared medullary canal for pressurization of bone cement is provided. The method includes the step of providing the prepared medullary canal, a cement injection device having a guide portion, and a pressurizer apparatus. The prepared medullary canal is defined by an end having a lip that defines an opening to the prepared medullary canal. The pressurizer apparatus has a first surface, a second surface spaced apart from the first surface, and an inner surface defining a channel extending between the first and second surfaces. The method further includes the steps of positioning one of the surfaces of the pressurizer apparatus on the lip of the prepared medullary canal, and inserting the guide portion of the cement injection device into the channel to create a substantial seal between the inner surface of the pressurizer apparatus and the guide portion and to permit the flow of bone cement from the guide portion into the medullary canal.

According to yet another embodiment of the present invention, a method is provided for substantially sealing prepared medullary canal for pressurization of bone cement. The method includes the step of providing a prepared medullary canal, a cement injection device having a guide portion, and a pressurizer apparatus. The prepared medullary canal includes a proximal end, an inner surface, and a lip adjacent the proximal end. The pressurizer apparatus has dissimilar exterior surfaces and an inner surface defining a channel between the dissimilar exterior surfaces. The method further includes the steps of selecting a dissimilar exterior surface of the pressurizer apparatus that is generally sized to form a substantial seal between the selected dissimilar exterior surface and the lip of the prepared medullary canal, positioning the selected dissimilar exterior surface on the lip of the prepared medullary canal, and inserting the guide portion of the cement injection device into the channel to create a substantial seal between the inner surface of the pressurizer apparatus and the guide portion and to permit the flow of bone cement from the guide portion into the medullary canal.

Additional features and advantages of the present invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 18 a cross-sectional view of yet another alternative embodiment of a pressurizer apparatus in accordance with the present invention situated upon another lip of a medullary canal showing the pressurizer apparatus including a body portion having an upper surface, a lower surface, a first end surface, a second end surface, a first inner surface defining a first channel extending between the upper and lower surfaces, a first pair of seals positioned to lie on the first inner surface, a second inner surface defining a second channel extending between the first and second end surfaces, and a second pair of seals positioned to lie on the second inner surface, the lower surface of the pressurizer apparatus being situated upon the lip of the prepared medullary canal and a guide portion of a cement injection device extending through the first channel into the prepared medullary canal to inject bone cement therein and engaging the first pair of seals;

DETAILED DESCRIPTION OF THE DRAWINGS

Figure 1:
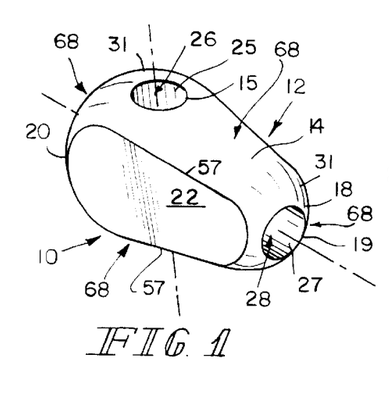
FIG. 1 is a perspective view of a pressurizer apparatus in accordance with the present invention showing the pressurizer apparatus including a body portion having an upper surface, a first inner surface defining a first channel extending through the upper surface, a lower surface, a first end surface, a second inner surface defining a second channel extending through the first end surface, a second end surface, and a substantially flat side wall extending between the upper and lower surfaces.
Figure 4:
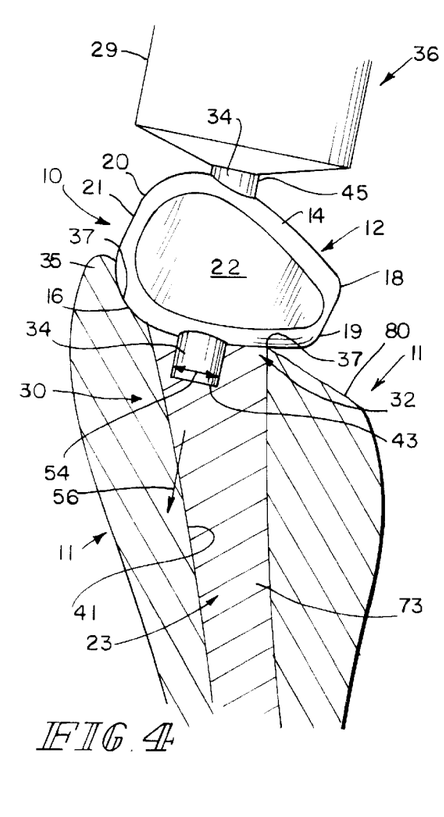
FIG. 4 is a side view of the pressurizer apparatus of FIG. 1 showing the lower surface of the pressurizer apparatus situated upon a lip of a first prepared medullary canal, with the prepared medullary canal in cross-section, and a guide portion of a cement injection device extending through the first channel and into the medullary canal to inject bone cement therein.

In accordance with the present invention, a pressurizer apparatus 10 is provided for sealing between a prepared medullary canal 30 of a femur 11 and a cement injection device 36 as shown, for example, in FIGS. 1 and 4. Pressurizer apparatus 10 includes a body portion 12 having a plurality of dissimilar exterior sealing surfaces 68. By providing several dissimilar exterior sealing surfaces 68, pressurizer apparatus 10 provides a range of sealing surfaces 68 in a single apparatus. Thus, according to the present invention, one pressurizer apparatus 10 is capable of sealing a size range greater than a single conventional pressurizer apparatus (not shown). Accordingly, only one pressurizer apparatus 10 is necessary to cover the size range of prepared medullary canals 30 previously sealed by the combined size range of several conventional pressurizer apparatus. Thus, only one pressurizer apparatus 10 needs to be present in the operating room and be manipulated by a surgeon.

According to the present invention, pressurizer apparatus 10 is formed to seal prepared medullary canal 30. Canal 30 is positioned to lie within femur 11 that includes a top surface 80 adjacent a proximal end 35 and a lip 37. Lip 37 defines a canal opening 32 into canal 30. In addition, canal 30 includes an inner surface 41 that defines a channel 23 that is sized to receive a stem of a prosthesis (not shown) therein. It is understood that prepared medullary canal 30 is prepared by removal of a head (not shown) of femur bone 11 and boring of medullary canal 30 in accordance with well known surgical techniques. While femur 11 is illustrated and described herein, it is understood that pressurizer apparatus 10 is suitable for use with a wide variety of bones that include a medullary canal that requires sealing for pressurizing action during surgery. As best shown in FIGS. 4–7, lips 37, 137, 237, 337 are formed in a variety of shapes and sizes. Moreover, dissimilar surfaces 68 of pressurizer apparatus 10 are configured to mate with lips 37, 137, 237, 337.

Pressurizer apparatus 10 cooperates with cement injection device 36. Cement injection device 36 includes a container portion 29 configured to receive bone cement 73 therein and a guide portion 34 in communication with container portion 29. Guide portion 34 includes a slightly proximal end 45 adjacent container portion 29, a distal end 43 spaced apart from proximal end 45, and a passageway (not shown) therebetween. Guide portion 34 has a diameter 54 sized to permit flow of bone cement 73 therethrough. Although cement injection device 36 is illustrated and described, it is understood that a wide variety of flow direction devices may be used in accordance with the present invention.

As shown in FIG. 1, body portion 12 of pressurizer apparatus 10 has four dissimilar exterior sealing surfaces 68 including an upper surface 14, a lower surface 16, a first end surface 18, and a second end surface 20. Upper and lower surfaces 14, 16 have opposite ends 31 and opposite edges 57 extending between the opposite ends 31. Dissimilar exterior sealing surfaces 68 are all generally hemispherically shaped. The term "generally hemispherical" as used through the specification and claims is intended to cover convex surfaces that may or may not have a uniform radius and may be more or less than half a sphere. For example, upper surface 14 may have a generally uniform radius from its focus or that radius may vary in length at different positions on upper surface 14. By providing several dissimilar exterior sealing surfaces 68, pressurizer apparatus 10 provides a range of sealing surfaces. Thus, only one pressurizer apparatus 10 needs to be manufactured and shipped, to be present in the operating room, and to be manipulated by a surgeon.

Figure 2:
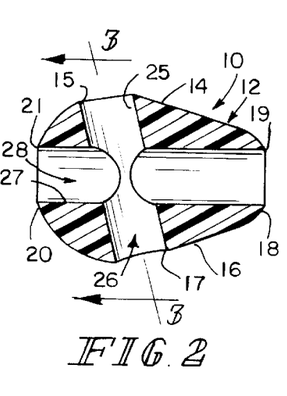
FIG. 2 is a cross-sectional view of the pressurizer apparatus of FIG. 1 showing the first inner surface of the body portion defining the first channel extending between the upper and lower surfaces and the second inner surface defining the second channel intersecting the first channel and extending between the first and second end surfaces.
Figure 3:
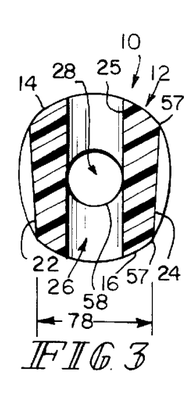
FIG. 3 is a cross-sectional view taken along lines 3—3 of FIG. 2 showing opposing substantially flat side walls extending between opposite side edges of the upper and lower surfaces.

Body portion 12 also includes a first side wall 22 and a second side wall 24 spaced apart from first side wall 22 and extending between the opposite edges 57 of surfaces 14, 16. First and second side walls 22, 24 are spaced apart a distance shown by arrow 78 adjacent lower surface 16. While side walls 22, 24 appear to be substantially flat, it is understood that the shape and size of side walls 22, 24 may vary in accordance with the present invention. As shown, for example, in FIGS. 2 and 3, body portion 12 further includes a first inner surface 25 defining a first or dissimilar-surface channel 26 that extends between upper surface 14 and lower surface 16 and a second inner surface 27 defining a second or end-surface channel 28 extending between first and second end surfaces 18, 20. Inner surface 25 further defines opening 15 into channel 26 through upper surface 14 and opening 17 into channel 26 through lower surface 16. Inner surface 27 defines opening 19 into channel 28 through first end surface 18 and opening 21 into channel 28 through second end surface 20. First and second inner surfaces 25, 27 intersect to form a junction 58 as shown, for example, in FIG. 2. According to the present invention, four dissimilar exterior sealing surfaces 68 are provided, but fewer or more dissimilar sealing surfaces are also within the scope and spirit of the present invention as will be discussed in greater detail below. According to the present invention, openings 15, 17, 19, and 21 to first and second inner surfaces 25, 27 are sized to be larger than the largest guide portion 34 of cement injection devices 36. This permits easier insertion of guide portion 34 into either first or second channels 26, 28. First inner surface 25 and second inner surface 27 are sized to mate with guide portion 34 of cement injection device 36 to form a seal between guide portion 34 and pressurizer apparatus 10.

To use pressurizer apparatus 10 during the pressurization process, a surgeon or other medical personnel (not shown) first selects an appropriate dissimilar exterior sealing surface 68 that substantially covers canal opening 32 of prepared medullary canal 30 to seal with lip 37 of femur 11. For example, as shown in FIG. 4, lower surface 16 has been selected and the guide portion 34 of cement injection device 36 has been inserted into channel 26 of body portion 12.

Figure 5:
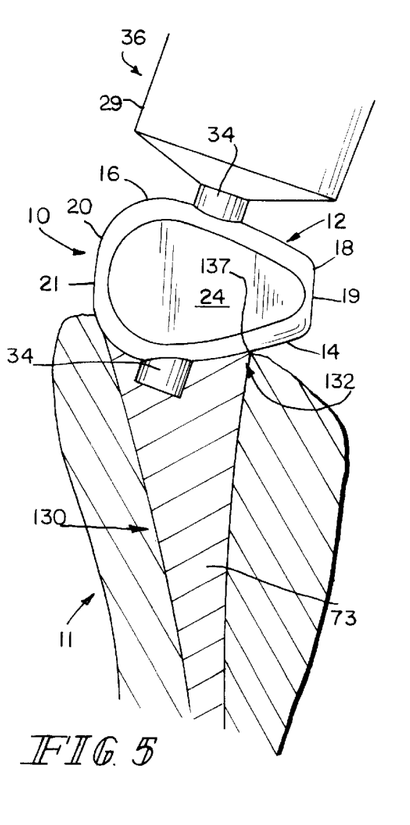
FIG. 5 is a side view similar to FIG. 4 showing the upper surface of the pressurizer apparatus situated upon a lip of a second prepared medullary canal and the guide portion of the cement injection device extending through the first channel and into the second medullary canal.
Figures 6, 7, 18:
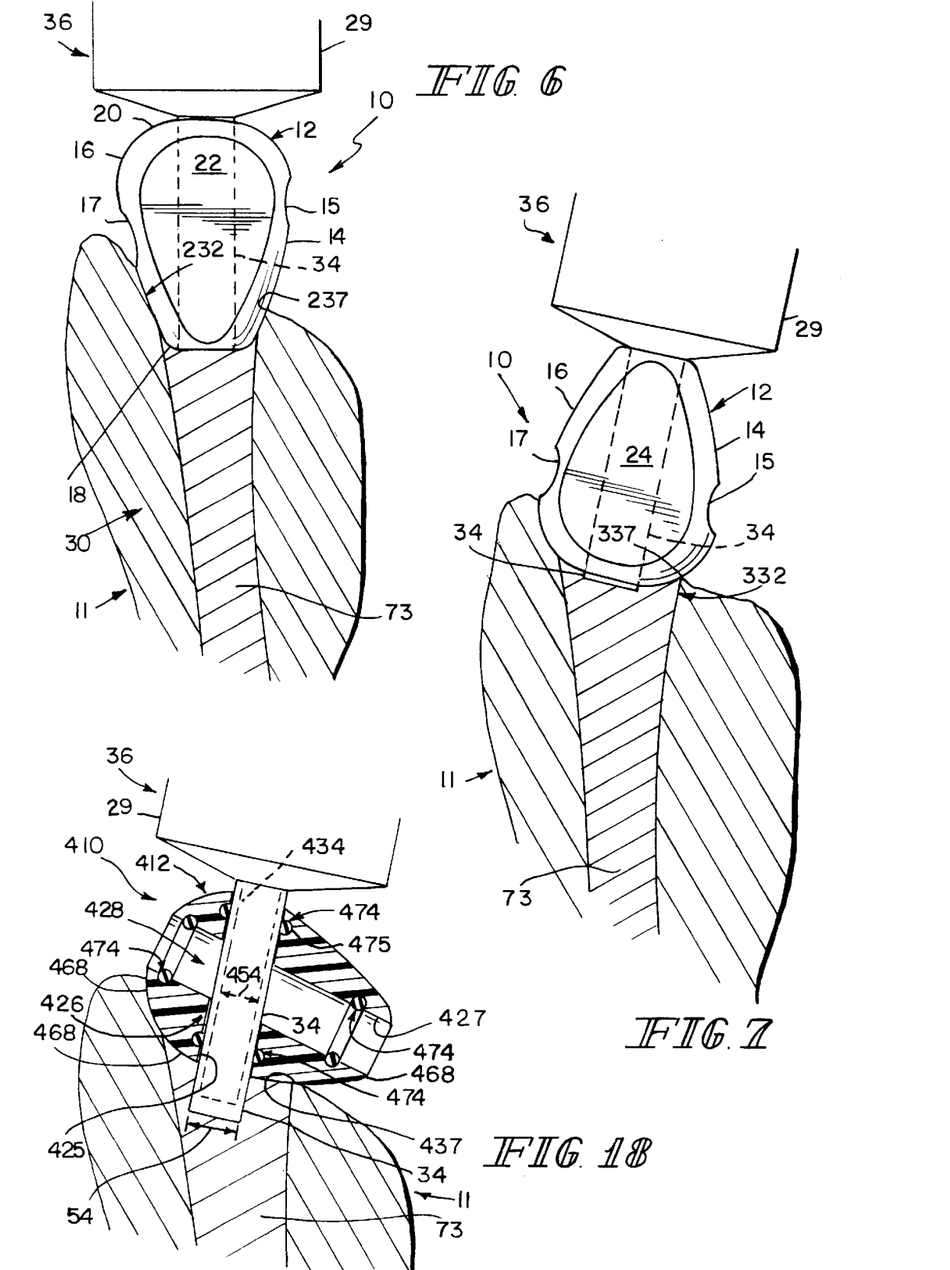
FIG. 6 is a side view similar to FIG. 4 showing the first end surface of the pressurizer apparatus situated upon a lip of a third prepared medullary canal and the guide portion extending through the second channel and into the third medullary canal.
FIG. 7 is a side view similar to FIG. 4 showing the second end surface of the pressurizer apparatus situated upon a lip of a fourth prepared medullary canal and the guide portion extending through the second channel and into the fourth medullary canal.

The surgeon may then grip side walls 22, 24 and place lower surface 16 on lip 37 of prepared medullary canal 30. As shown in FIG. 5, a surgeon has selected upper surface 14 of body porion 12 to engage lip 137 of a prepared medullary canal 130. As shown, for example, in FIGS. 6 and 7, the surgeon has selected first and second end surfaces 18, 20 to engage lips 237, 337, respectively. Canals 130, 230, 330 and lips 137, 237, 337 have a size and shape that is different from canal 30 and lip 37. It is also understood that while lower surface 16, lip 37, and canal 30 will be described hereafter, upper surface 14 and first and second end surfaces 18, 20 of pressurizer apparatus 10 may also close prepared medullary canals 130, 230, 330 and seal canal openings 132, 232 and 332, respectively.

Pressurizer apparatus 10 by cooperating with cement injection device 36 and engaging lip 37 to create a seal therebetween, permits bone cement 73 to more completely fill the intricacies of inner wall 41 of prepared medullary canal 30. Pressurizer apparatus 10 creates a seal between one of the dissimilar sealing surfaces 68 and lip 37. Engagement between body porion 12 and lip 37 allows inner surface 41 to be exposed to and pressurized by bone cement 73 to increase the effectiveness of the cement mantle. Likewise, because pressurizer apparatus 10 engages lip 37, little if any bone cement 73 bleeds past lip 37 on to top surface 80 of femur 11. The shape of dissimilar sealing surfaces 68 permits pressurizer apparatus 10 to seal on lip 37. Thus, a generally thin or linear seal is formed between pressurizer apparatus 10 and prepared medullary canal 30 by placing a dissimilar sealing surface 68 over the canal opening 32 on lip 37.

Having sealed canal opening 32 of prepared medullary canal 30 with pressurizer apparatus 10 and cement injection device 36, the surgeon then injects bone cement 73 from container portion 29 through guide portion 34 and into channel 23 of prepared medullary canal 30. Thus, the surgeon is able to pressurize prepared medullary canal 30 with bone cement 73.

Because canal opening 32 has been sealed by lower surface 16 of pressurizer apparatus 10 and because guide portion 34 of cement injection device 36 has closed channel 26, pressure from cement injection device 36 is transmitted through guide portion 34 into prepared medullary canal 30 and forces bone cement 73 into intricacies (not shown) of inner surface 41 of prepared medullary canal 30. Thus, bone cement 73 is interdigitated into the cancellous structure of inner surface 41 of prepared medullary canal 30 to provided an optimal cement mantle for placement of a prosthetic device (not shown) such as a stem of a hip prothesis.

This ability to select a different dissimilar exterior sealing surface 68 for differently sized and shaped canal openings 32, 132, 232, 332 within one pressurizer apparatus 10 allows for a reduction in the number of pressurizer apparatus 10 necessary to be included in a prosthetic replacement kit (not shown) to adequately seal various sizes of canal openings 32, 132, 232, 332. Dissimilar exterior sealing surfaces 68 also eliminate the need for multiple conventional pressurizer apparatus and thus saves cost in both producing and shipping numerous pressurizer apparatus in each hip replacement kit. It is understood that pressurizer apparatus 10 in accordance with the present invention are suitable for use with replacement kits such as kits designed for use with a hip, a shoulder, a knee, or any bone having a canal therein that requires pressurization for the insertion of bone cement during surgery. It is also understood that pressurizer apparatus 10 is suitable for production and shipment as a single unit separate from a replacement kit.

Alternative embodiments in accordance with the present invention are shown in FIGS. 8–25. All numbering of pressurizer apparatus 110, 210, 310, 410, 510, 610, 710, 810, 910 as will be discussed hereafter correspond to those numerals previously described for pressurizer apparatus 10 unless otherwise indicated.

Figure 8:
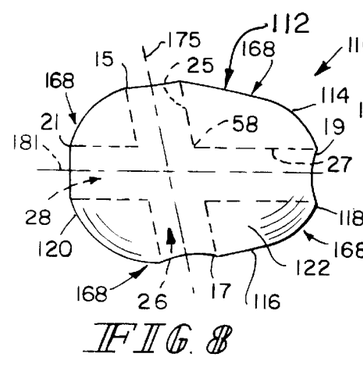
FIG. 8 is a side view of an alternative embodiment of a pressurizer apparatus in accordance with the present invention showing the pressurizer apparatus including a body portion having dissimilar upper and lower surfaces, a first end surface, a second end surface, a first inner surface, in phantom, defining a first channel extending between the dissimilar upper and lower surfaces and a second inner surface, in phantom, defining a second channel extending between the first and second end surfaces.
Figures 9, 10:
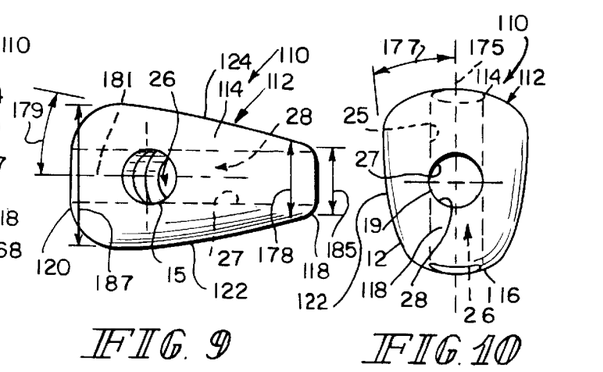
FIG. 9 is a top view the pressurizer apparatus of FIG. 8 showing the second channel, in phantom, extending between the first and second end surfaces and the first channel extending between the dissimilar upper and lower surfaces.
FIG. 10 is an end view of the pressurizer apparatus of FIG. 8 showing the first channel, in phantom, extending between the dissimilar upper and lower surfaces and the second channel extending between the first and second end surfaces.

As shown in FIGS. 8–10, a pressurizer apparatus 110 is provided. Pressurizer apparatus 110 includes a body portion 112 having a plurality of dissimilar exterior sealing surfaces 168. Body portion 112 has four such dissimilar exterior sealing surfaces 168 including an upper surface 114, a lower surface 116, a first end surface 118, and a second end surface 120. Body portion 112 also includes a first side wall 122 and a second side wall 124 spaced apart from first side wall 122. As shown in FIG. 9, first and second side walls 122, 124 are spaced apart a distance 178 therebetween adjacent end surface 118. Side walls 122, 124 are substantially flat. It is understood that side walls 122, 124 may be formed in a variety of shapes and in accordance with the present invention.

Distance 178 between side walls 122, 124 of pressurizer apparatus 110 is less than that of distance 78 between side walls 22, 24 of pressurizer apparatus 10. See FIG. 3. Therefore, dissimilar exterior sealing surfaces 168 of pressurizer apparatus 110 are different than those of pressurizer apparatus 10. As shown in FIG. 10, lower surface 116 has a different profile than upper surface 114.

Side walls 122, 124 converge from upper surface 114 toward lower surface 116. As shown in FIG. 10, side walls 122, 124 converge at an angle of about 10 degrees, as illustrated by arrow 177, relative to a central axis 175 running through body portion 112. In addition, as shown in FIG. 9, side walls 122, 124 converge from second end surface 120 toward first end surface 118 at an angle of about 12 degrees, as illustrated by arrow 179, relative to horizonal axis 181 extending through body portion 112. First end surface 118 has a first lateral width 185 while second end surface 120 has a second lateral width 187 that is greater than first lateral width 185 of first end surface 118. Illustratively, the ratio of first lateral width 185 to second lateral width 187 is about 1.9:1. It is understood that this ratio may vary in accordance with the present invention.

Figures 11, 12, 13:
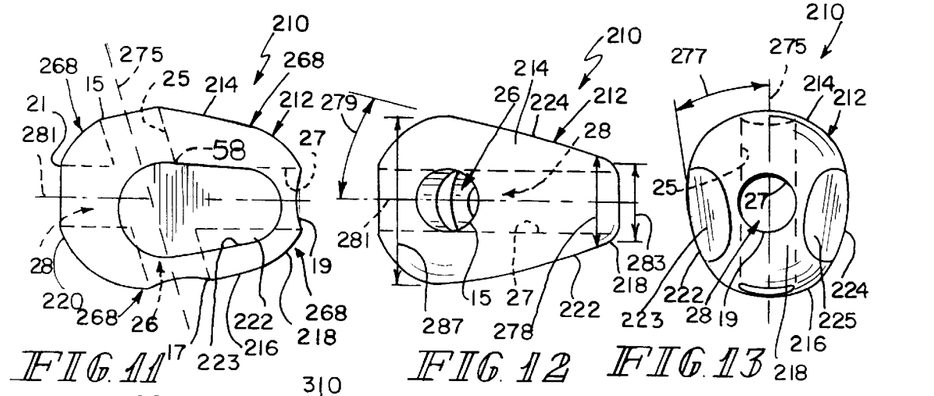
FIG. 11 is a side view of yet another alternative embodiment of a pressurizer apparatus in accordance with the present invention showing the pressurizer apparatus including a body portion having upper and lower surfaces having opposite ends, first and second end surfaces extending between the opposite ends, a dimpled side wall extending between the upper and lower surfaces, a first inner surface, in phantom, defining a first channel and a second inner surface, in phantom, defining a second channel.
FIG. 12 is a top view of the pressurizer apparatus of FIG. 11 showing the second channel, in phantom, extending between the first and second end surfaces, and the first channel extending between the upper and lower surfaces.
FIG. 13 is an end view of the pressurizer apparatus of FIG. 11 showing the first channel, in phantom, extending between the upper and lower surfaces, the second channel extending between the first and second end surfaces, and dimples formed in opposing side walls.

Similarly, yet another embodiment of a pressurizer apparatus 210 is shown in FIGS. 11–13. Pressurizer apparatus 210 includes a body portion 212 having a plurality of dissimilar exterior sealing surfaces 268. Body portion 212 has four such dissimilar exterior sealing surfaces 268 including an upper surface 214, a lower surface 216, a first end surface 218, and a second end surface 220. Body portion 212 also includes first and second side walls 222, 224 that are formed to include a first dimple 223 and a second dimple 225 spaced apart from first dimple 223. First and second side walls 222, 224 are spaced apart a distance 278 therebetween adjacent end surface 218. See FIG. 12. Distance 278 between first and second side walls 222, 224 of pressurizer apparatus 210 is greater than distance 78 between side walls 22, 24 of pressurizer apparatus 10. See FIG. 3. Dimples 223, 225 are concave and side walls 222, 224 converge from upper surface 214 toward lower surface 216. Illustratively, side walls 222, 224 converge at an angle of about 13 degrees, as illustrated by arrow 277, relative to a central axis 275 running through body portion 212. In addition, as shown in FIG. 12, side walls 222, 224 converge from second end surface 220 toward first end surface 218 at an angle 279 of about 17 degrees relative to a horizontal axis 281 extending through body portion 212.

First end surface 218 has a first lateral width 283 while second end surface 220 has a second lateral width 287 that is greater than first lateral width 283. Illustratively, the ratio of first lateral width 283 to second lateral width 287 is about 1.3:1. As with pressurizer apparatus 10 and 1 10, pressurizer apparatus 210 substantially seals canal openings 32 of a different size range or contour of prepared medullary canals 30.

As demonstrated by pressurizer apparatus 10, 110, 210, dissimilar exterior sealing surfaces 68, 168, 268 of each pressurizer apparatus 10, 110, 210 can be designed to be different from each other to cover an almost infinite configuration of canal openings.

Differences in sealing surfaces 68, 168, 268 allow for even wider ranges of canal openings 32 to be substantially sealed by providing pressurizer apparatus 10, pressurizer apparatus 110, and pressurizer apparatus 210 in a hip replacement kit. Therefore, three pressurizer apparatus 10, 110, 210 include twelve dissimilar exterior sealing surfaces 68, 168, 268. Whereas, twelve conventional pressurizer apparatus would be required to seal a corresponding size range of prepared medullary canals as sealed by pressurizer apparatus 10, 110, 210 of the present invention.

In yet another embodiment of the present invention, a pressurizer apparatus 310 has the ability to seal more than one size of guide portion 34 of cement injection device 36. See FIGS. 14–16. Pressurizer apparatus 310 includes a body portion 312 having a plurality of dissimilar exterior sealing surfaces 368. Body portion 312 has four such dissimilar exterior sealing surfaces 368 including an upper surface 314, a lower surface 316, a first end surface 318, and a second end surface 320. Body portion 312 also includes first and second side walls 222, 224.

Figure 14:
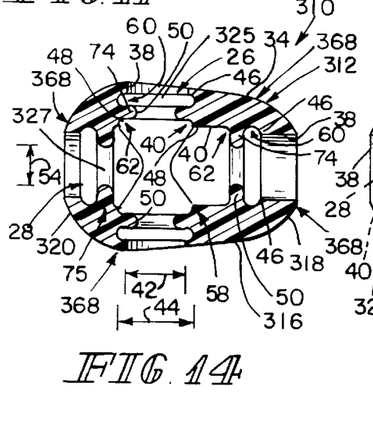
FIG. 14 is a cross-sectional view of an alternative embodiment of a pressurizer apparatus in accordance with the present invention showing the pressurizer apparatus including a body portion having an upper surface, a lower surface, a first end surface, a second end surface, a first inner surface defining a first channel extending between the upper and lower surfaces, a pair of seals positioned to lie on the first inner surface, a second inner surface defining a second channel extending between the first and second end surfaces, and second pair of seals positioned to lie on the second inner surface.
Figures 15, 16:
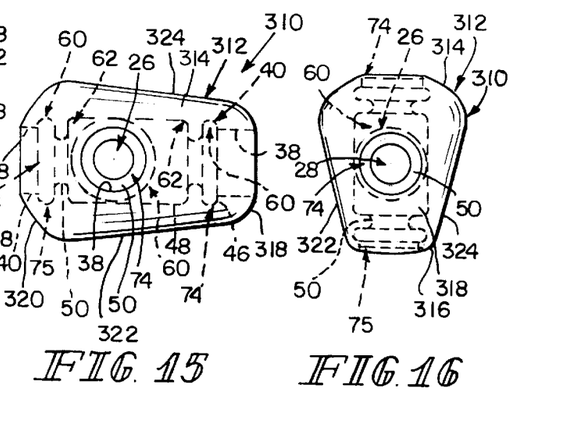
FIG. 15 is a top view of the pressurizer apparatus of FIG. 14 showing the second channel, in phantom, extending between the first and second end surfaces, a pair of seals extending into the second channel, and a seal positioned to lie in the first channel.
FIG. 16 is an end view of the pressurizer apparatus of FIG. 14 showing the first channel, in phantom, extending between the upper and lower surfaces, a pair of seals extending into the first channel, and a seal positioned to lie in the second channel.

Body portion further includes a first inner surface 325 and a second inner surface 327 defines two sets of seals 74, 75 respectfully. One seal 74 is positioned to lie between junction 58 and upper surface 14 and seal 75 is positioned to lie between junction 58 and lower surface 16. Likewise, one seal 74 of second set is positioned to lie between junction 58 and first end surface 18 and seal 75 is positioned to lie between junction 58 and second end surface 18. Therefore, seals 74,75 provide a sealing means for openings 15, 17, 19, 21 upon extension of the guide portion through channels 26, 28, respectively.

Seals 74, 75 include a first wall 38 and a second wall 40 that are incorporated within channel 26 as shown, for example, in FIG. 14. First wall 38 has a first diameter 42 and second wall 40 has a second diameter 44 that is greater than first diameter 42 of first wall 38. Second wall 40 further includes a first end 46, a second end 48 spaced apart from first end 46, and a tab 50 extending into channel 26 as shown, for example, in FIGS. 14–16. A first indented portion 60 is situated to lie between first end 46 and tab 50 and a second indented portion 62 is situated to lie between second end 48 and tab 50. According to the present invention, tab 50 is rounded and sized to flex into indented portions 60, 62 during insertion of guide portion 34 through channel 26. Moreover, it is understood that the shape of tabs 50 and indented portions 60, 62 may vary in accordance with the present invention.

Body portion 12 is made of a resilient material such as silicone rubber. This flexibility allows exterior sealing surfaces 68 to yield to the more rigid bone 11. Also, tab 50 yields to more rigid guide portion 34 of cement injection device 36 and moves into indented portions 60, 62 respectively since a diameter 52 of tab 50 is less than diameter 54 of guide portion 34. Furthermore, because the resilient material allows tab 50 to yield over a range of various diameters of guide portions, tab 50 will seal a size range of guide portions of cement injection devices. Pressurizer 310 of the present invention will therefore not only seal a predetermined range of canal openings 32, but will also accommodate a range of diameters of guide portions of cement injection devices therein.

Figure 17:
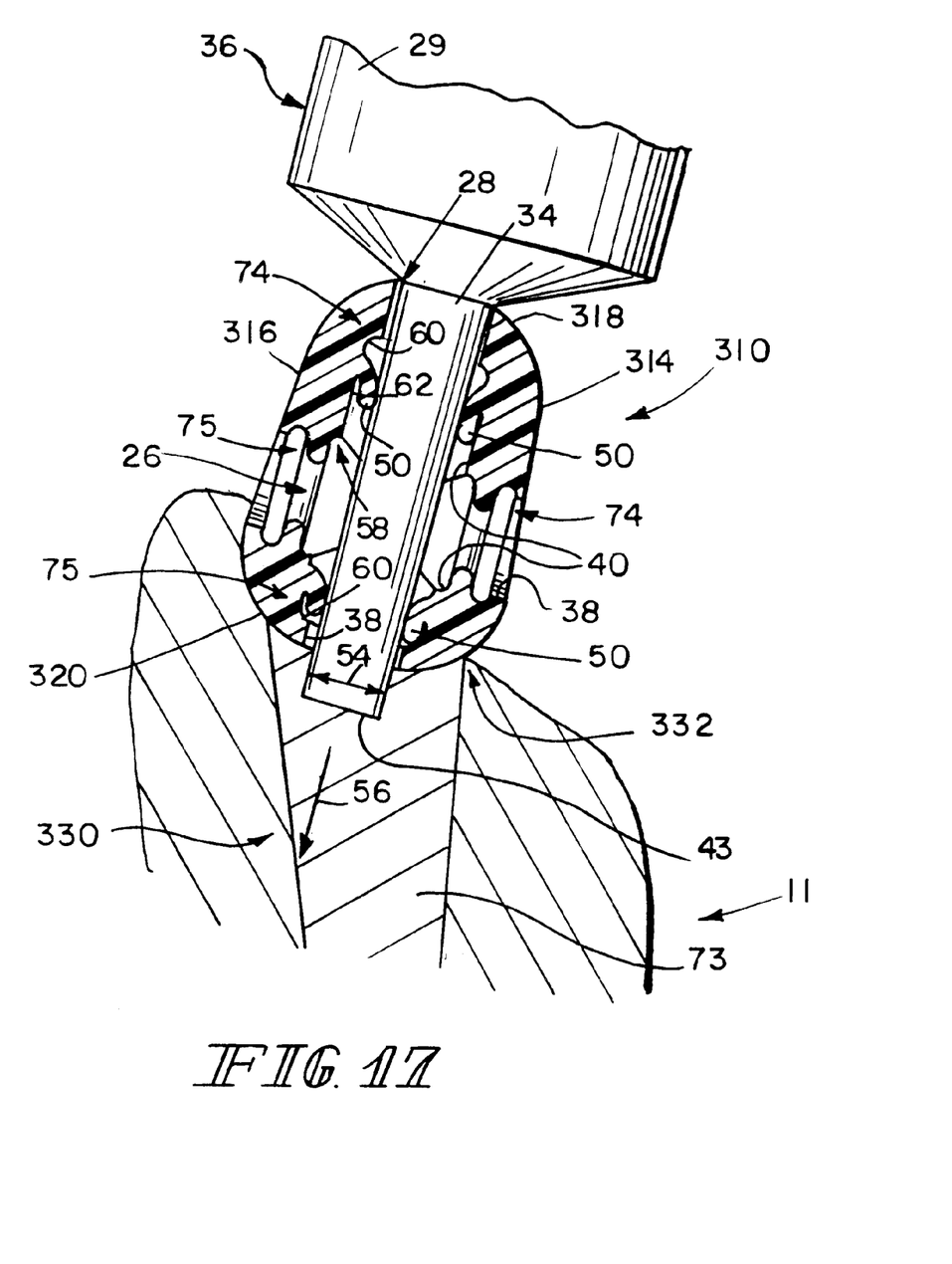
FIG. 17 is a cross-sectional view of the pressurizer apparatus of FIG. 14 showing the second end surface of the pressurizer apparatus situated upon a lip of a prepared medullary canal and a guide portion of a cement injection device extending through the second channel into the prepared medullary canal to inject bone cement therein and engaging the second pair of seals.

As shown in FIG. 17, opening 19 is sealed off from junction 58 by tab 50 of seal 74 while guide portion 34 is inserted into second channel 28. Similarly, opening 21 is sealed off from junction 58 by tab 50 of seal 75 while guide portion 34 is inserted into second channel 28. As shown in FIG. 17, tabs 50 positioned to lie near first and second end surfaces 18, 20 have swayed in a guide portion insertion direction 56 to partially or fully fill second and first indented portions 62, 60 of second wall 40, respectively.

By being able to flex into second and first indented portions 62, 60, tabs 50 have additional room to sway and thus present less resistance to guide portion 34 during insertion and removal of said guide portion 34 from pressurizer apparatus 310. Thus, this movement of tabs 50 allows a surgeon or other medical personnel to more easily start the insertion and guidance of guide portion 34 into the pressurizer apparatus 310. Likewise, the rounded nature of tab 50 reduces the amount of surface contact that tab 50 makes with guide portion 34. This reduced surface contact further reduces resistance of pressurizer apparatus 310 during insertion of guide portion 34.

The sway of tabs 50 also permits the use of cement injection devices 36 having guide portions with different diameters. The amount of sway of tabs 50 will increase proportionality with an increase in diameter size of the guide portion of cement injection device 36. Thus, if a guide portion (not shown) having a diameter less than diameter 54 is used to inject bone cement 73 into prepared medullary canal 330, tabs 50 will sway slightly into first and second intended portions 60, 62 to seal second channel 28. If, however, a guide portion (not shown) having a diameter greater than diameter 54 is used to inject bone cement 73, tabs 50 will sway to a greater extent into first and second indented portions 60, 62 and also seal second channel 28.

According to the present invention, guide portion 34 may be inserted in first and second end surfaces 18, 20 and upper and lower surfaces 14, 16 to move tab 50 in indented portions 60, 62. As previously mentioned, this movement reduces the resistance asserted on guide portion 34 by tab 50 and allows medical personnel to more easily insert guide portion 34 through first or second channels 26, 28. In addition the sway of tabs 50 allows medical personal to use different guide portions 34 of various diameters.

According to yet another embodiment of the present invention, a pressurizer apparatus 410 includes a body portion 412 having first and second inner surfaces 425, 427 defining channels 426, 428 and seals 474. See FIG. 18. Seals 474 are formed as O-rings 475 and are integrally attached to body portion 412. When guide portion 34 of cement injection device 36 is inserted through channels 426, 428, O-ring 475 yields to form a seal around guide portion 34. Seals 474 along with the sealing provided by dissimilar exterior sealing surfaces 468 against lip 437 provides a seal between guide portion 34 and canal opening 432 of prepared medullary canal 430. Seals 474 are formed to engage guide portions having various diameters. For example, as shown in phantom in FIG. 18, seals 474 are configured to engage a guide portion 434 having a diameter 454 that is less than diameter 54 of guide portion 34.

Figures 19, 20:
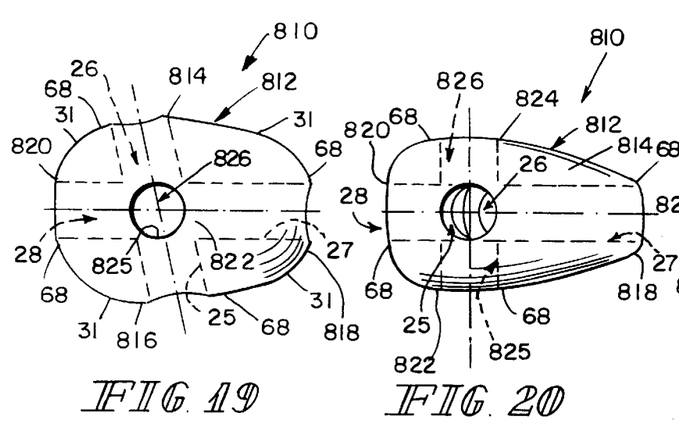
FIG. 19 is a side view of yet another alternative embodiment of a pressurizer apparatus in accordance with the present invention showing the pressurizer apparatus including a body portion having an upper surface, a lower surface, a first end surface, a second end surface, a side surface, a first inner surface, in phantom, defining a first channel, a second inner surface, in phantom, defining a second channel extending between the first and second end surfaces, and a third inner surface defining a third channel extending through the side surface.
FIG. 20 is a top view of the pressurizer apparatus of FIG. 19 showing the first channel extending between the upper and lower surfaces, the second channel, in phantom, extending between the first and second end surfaces, and the third channel, in phantom, extending between first and second side surfaces.
Figure 21:
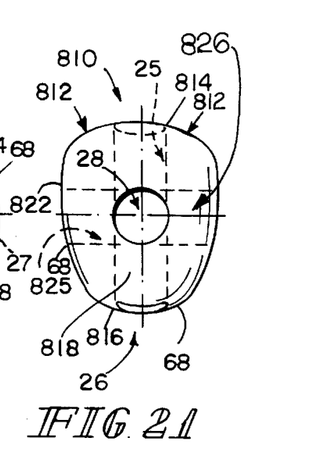
FIG. 21 is an end view of the pressurizer apparatus of FIG. 19 showing the first channel, in phantom, extending between the upper and lower surfaces, the second channel extending through one surface, and the third channel, in phantom, extending between the first and second side surfaces.
Figure 22:
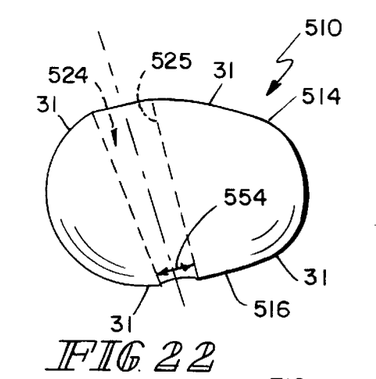
FIG. 22 is a side view of yet another embodiment of a pressurizer in accordance with the present invention showing the pressurizer apparatus including a body portion having an upper surface and a lower surface, and an inner surface, in phantom, defining a generally tapered channel converging from the upper surface toward the lower surface.
Figure 23:
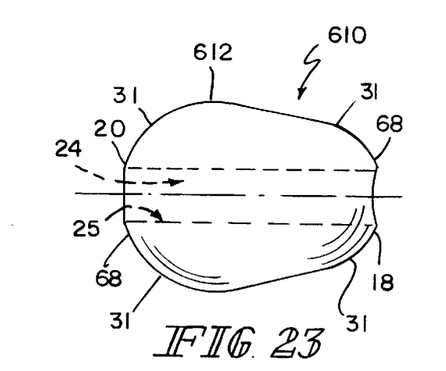
FIG. 23 is a side view of yet another embodiment of a pressurizer in accordance with the present invention showing the pressurizer apparatus including a body portion having a first end surface, a second end surface, and an inner surface, in phantom, defining a generally cylindrical channel extending between the first and second end surfaces.
Figure 24:
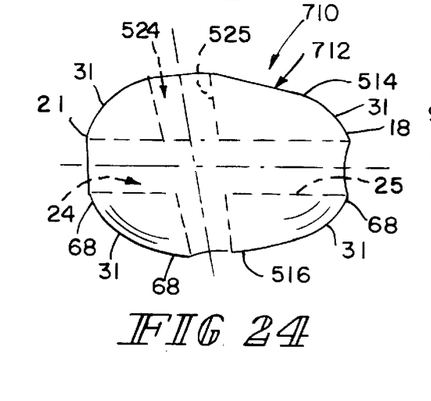
FIG. 24 is a side view of yet another embodiment of the present invention showing a pressurizer apparatus including a body portion having an upper surface, a lower surface, a first end surface, a second end surface, a first inner surface, in phantom, defining a generally tapered first channel converging from the upper end to the lower end and a second inner surface, in phantom, defining a generally cylindrical second channel extending between the first and second end surfaces.
Figure 25:
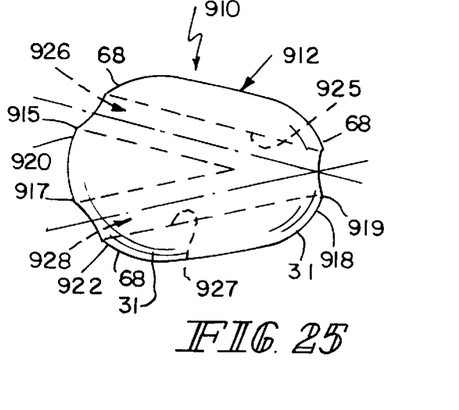
FIG. 25 is a side view of yet another embodiment of a pressurizer apparatus in accordance with the present invention showing the pressurizer apparatus including a body portion having a first end surface, a second end surface, a third end surface, a first inner surface, in phantom, defining a first channel extending between the first and second end surfaces, and a second inner surface, in phantom, defining a second channel extending between the third and second end surfaces.

According to yet another embodiment of the present invention, a pressurizer apparatus 810 is provided that includes a body portion 812 having a plurality of dissimilar exterior sealing surfaces 68. See FIGS. 19–21. Referring now to FIG. 19, dissimilar exterior sealing surfaces 68 include an upper surface 814, lower surface 816, a first end surface 818, and a second end surface 820. FIG. 20 illustrates a first side surface 822, and a second side surface 824 that are generally hemispherical in shape. Body portion 812 further includes first inner surface 25 defining first channel 26, second inner surface 27 defining second channel 28, and third inner surface 825 defining a third channel or side wall channel 826. See FIG. 19. As best shown in FIG. 20, in phantom, third channel 826 extends between first and second side surfaces 822, 824. Thus, pressurizer apparatus 810 can seal six size ranges of channel openings 32. It is understood that pressurizer apparatus that include additional channels extending therethrough are also within the scope spirit of the present invention.

According to yet another embodiment of the present invention, a pressurizer apparatus 510 is provided that includes an upper surface 514, an opposite lower surface 516, and an inner surface 525 extending between upper and lower surfaces 514, 516. Inner surface 525 defines a tapered channel 524. See FIG. 22. Inner surface 525 is generally tapered to accept a tapered guide portion (not shown) to form an effective seal therebetween. Inner surface 525 can also seal guide portion 34 where diameter 54 of guide portion 34 is slightly greater than a diameter 554 of channel 524 adjacent lower surface 516. It is understood that inner surface 525 will flex and give slightly to permit passage of guide portion 34 therethrough. Moreover, it is understood that the angle of the taper may vary in accordance with the present invention. Further, tapered channel 524 may extend between various surfaces of pressurizer apparatus 510.

Pressurizer apparatus 10, 110, 210, 310, 410, 510, 810 can have any combination of generally cylindrical channels 26, 28, generally tapered channels 524, or generally cylindrical channels 26, 28 with seals 74, 75, or any other combination of features mentioned herein. Thus, according to yet another embodiment of the present invention, a pressurizer apparatus 610 is provided that includes a body portion 612 having dissimilar sealing surfaces 68 and inner surface 25 that defines channel 24 therebetween. See FIG. 23. Dissimilar sealing surfaces 68 include first end surface 18 and second end surface 20 with channel 24 extending therebetween. Thus, pressurizer apparatus 610 can seal two size ranges of canal openings 32.

In still another embodiment of the present invention, a pressurizer apparatus 710 is provided that includes a body portion 712 having plurality of dissimilar sealing surfaces 68. See FIG. 24. Dissimilar sealing surfaces 68 include upper surface 514, lower surface 516, first end surface 18, and second end surface 20. In addition, inner surface 25 defines generally cylindrical channel 24 and second inner surface 525 defines generally tapered channel 524 as shown, for example, in FIG. 24. Tapered channel 524 converges between upper surface 514 and lower surface 516. Thus, pressurizer apparatus 710 can seal three size ranges of canal openings 32. It is understood that channels 24 and 524 are interchangeable. As previously mentioned any combination of generally cylindrical channels, generally tapered channels, or other features of the invention can be used according to the present invention. Thus, pressurizer apparatus in accordance with the present invention can be configured to seal from one to six or more size ranges of canal openings.

According to yet another embodiment of the present invention, a pressurizer apparatus 910 is provided that includes a body portion 912 having plurality of dissimilar exterior sealing surfaces 68. See FIG. 25. Dissimilar sealing surfaces 68 include a first end surface 918, a second end surface 920, and a third end surface 922 that are generally hemispherical-shaped. Body portion 912 further includes a first inner surface 925 defining a first channel 926 that extends between first end surface 918 and second end surface 920. In addition, body portion 912 includes a second inner surface 927 defining a second channel 928 that extends between first end surface 918 and third end surface 922. See FIG. 25. First and second inner surfaces 925, 927 intersect to form a junction 958. Body portion 912 is also formed to include three openings 915, 917, 919. Opening 915 defines first channel 926 at second end surface 920, opening 917 defines second channel 928 at third end surface 922, and opening 919 defines first and second channels 926, 928 through first end surface 918. Pressurizer apparatus 910 can therefore seal three size ranges of canal openings 32 of prepared medullary canals 30 by inserting guide portion 34 of cement injection device into either of opening 915, 917, 919 and using first, second, or third end surfaces 918, 920, 922 to seal with lips (not shown) of prepared medullary canals (not shown). Channels 926, 928 can also be formed in body portion 912 so that they do not intersect as can the other pressurizer apparatus with multiple channels in accordance with the present invention.

Although this invention has been described in detail with reference to certain embodiments, innovations and modifications exist when the scope and spirt of the invention as described and as defined in the following claims.

I claim:

1. A pressurizer apparatus suitable for substantially sealing proximal ends of prepared medullary canals during pressurization with a cement injection device, the pressurizer apparatus comprising a body portion including dissimilar surfaces on opposed ends formed to engage the proximal ends, each surface including dissimilar surfaces and a dissimilar-surface channel extending between the dissimilar surfaces, the dissimilar-surface channel being sized and adapted to receive at least a portion of the cement injection device therein from either end of the channel.

2. The pressurizer apparatus of claim 1, wherein the body portion is formed to include spaced apart first and second end surfaces positioned to lie adjacent the opposite ends and an end-surface channel extending between the first and second end surfaces.

3. The pressurizer apparatus of claim 2, wherein the first and second end surfaces are dissimilar in shape and formed to engage the proximal ends of prepared medullary canals.

4. The pressurizer apparatus of claim 2, wherein the dissimilar-surface and end-surface channels intersect one another within the body portion.

5. The pressurizer apparatus of claim 1, wherein the dissimilar surfaces include opposite side edges and the body portion further includes spaced-apart side walls extending between the side edges of the dissimilar surfaces.

6. The pressurizer apparatus of claim 1, wherein the dissimilar-surface channel is defined by an inner surface having a seal that extends radially inwardly into the dissimilar-surface channel and is sized to engage the cement injection device.

7. A pressurizer apparatus of claim 1, wherein
one dissimilar surface is a generally convex-shaped first surface formed to engage a lip of the medullary canal, a another dissimilar surface is second surface spaced apart from the first surface, and a channel extending between the first surface and the second surface, the dissimilar-surface channel being sized to receive a guide portion of the cement injection device therethrough.

8. The pressurizer apparatus of claim 7, wherein the second surface is generally convex in shape.

9. The pressurizer apparatus of claim 8, wherein the body portion is formed to include opposite surfaces positioned to lie spaced apart from one another and an opposite surface channel extending between the opposite end surfaces.

10. The pressurizer apparatus of claim 9, wherein the opposite channel and the dissimilar surface channel intersect one another within the body portion.

11. The pressurizer apparatus of claim 9, wherein the opposite channel and dissimilar surface channel are each defined by an inner surface having a seal extending radially inwardly into the channel and the end-surface channel respectively and the seal is sized to engage the guide portion of the cement injection device.

12. The pressurizer apparatus of claim 7, wherein the dissimilar-surface channel is defined by an inner surface converging from the second surface toward the first surface.

13. The pressurizer apparatus of claim 7, wherein the dissimilar-surface channel is defined by an inner surface having a seal that extends radially inwardly into the channel and is sized to engage the guide portion of the cement injection device.

14. A pressurizer apparatus of claim 1, wherein
the body portion surfaces include an exterior surface formed to engage the proximal end and an inner surface defining a first wall having a first diameter, a second wall having a second diameter greater than the first diameter, and at least one channel extending through the exterior surface and incorporating the first and second walls, the second wall having a first end, a second end spaced apart from the first end, and a tab extending into the channel and positioned to lie between the first and second ends of the second wall.

15. The pressurizer apparatus of claim 14, wherein the tab is rounded.

16. The pressurizer apparatus of claim 14, wherein the second wall defines a first portion positioned to lie between the tab and the first end of the second wall and a second portion positioned to lie between the tab and the second end of the second wall, and the first and second portions are sized to receive at least a portion of the tab therein during extension of the guide portion through the channel.

17. A method of sealing a prepared medullary canal for pressurization of bone cement, the method including the steps of
providing the prepared medullary canal including an end having a lip defining an opening to a canal therethrough, a cement injection device having a guide portion, and a pressurizer apparatus having at one end a first surface, a second surface spaced apart from the first surface, and an inner surface defining a channel extending between the first and second surfaces, and at another end a third surface, a fourth surface spaced apart from the third surface and second channel extending between the third and fourth surfaces, positioning one pair of the first and second surfaces or third and fourth surface on the lip of the prepared medullary canal, and inserting the guide portion of the cement injection device into the channel extending between the one pair of surfaces to create a substantial seal between the inner surface of the pressurizer apparatus and the guide portion and to permit the flow of bone cement from the guide portion and into the medullary canal.

18. The method of claim 17, wherein the first surface is generally convex-shaped.

19. The method of claim 17, wherein the method further includes the step of selecting one of the pairs of first and second or third and fourth surfaces of the pressurizer apparatus that is generally suited to cover the prepared medullary canal and form a substantial seal between the pressurizer apparatus and the lip of the prepared medullary canal and the positioning step includes the step of positioning the selected pair of surfaces over the prepared medullary canal.

20. The method of claim 17, wherein the pressurizer apparatus includes a pair of spaced apart seals extending into the channel and the seals are sized for engagement with the guide portion.

* * * * *